United States Patent
Tsukada et al.

(10) Patent No.: US 9,797,870 B2
(45) Date of Patent: Oct. 24, 2017

(54) LIQUID DELIVERY DEVICE AND CHEMICAL ANALYSIS APPARATUS USING LIQUID DELIVERY DEVICE

(71) Applicant: Hitachi, Ltd., Chiyoda-ku, Tokyo (JP)

(72) Inventors: Nobuhiro Tsukada, Tokyo (JP); Yoshihiro Nagaoka, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 300 days.

(21) Appl. No.: 14/751,965

(22) Filed: Jun. 26, 2015

(65) Prior Publication Data

US 2016/0054272 A1    Feb. 25, 2016

(30) Foreign Application Priority Data

Aug. 25, 2014   (JP) ................... 2014-170030

(51) Int. Cl.
*G01N 30/34*   (2006.01)
*G01N 30/02*   (2006.01)

(52) U.S. Cl.
CPC ........ *G01N 30/34* (2013.01); *G01N 2030/027* (2013.01); *G01N 2030/347* (2013.01)

(58) Field of Classification Search
CPC ........ G01N 2030/027; G01N 2030/347; G01N 30/34
See application file for complete search history.

(56) References Cited

U.S. PATENT DOCUMENTS

| | | | | |
|---|---|---|---|---|
| 8,438,911 | B2* | 5/2013 | Weissgerber | G01N 30/36 73/40.5 R |
| 2007/0000312 | A1* | 1/2007 | Weissgerber | G01N 30/36 73/61.56 |
| 2007/0000313 | A1* | 1/2007 | Weissgerber | G01N 30/36 73/61.56 |
| 2010/0083739 | A1* | 4/2010 | Weissgerber | G01N 30/36 73/61.56 |
| 2011/0259451 | A1* | 10/2011 | Weissgerber | G01N 30/36 137/565.11 |
| 2015/0268202 | A1* | 9/2015 | Gaita | G01N 30/32 210/198.2 |
| 2016/0108906 | A1* | 4/2016 | Wichmann | F04B 51/00 73/168 |

FOREIGN PATENT DOCUMENTS

JP    2005-274148 A    10/2005

* cited by examiner

*Primary Examiner* — John Fitzgerald
(74) *Attorney, Agent, or Firm* — Crowell & Moring LLP

(57) ABSTRACT

A chemical analysis apparatus includes a liquid delivery device and a liquid discharge unit discharging delivered liquids, the liquid delivery device including: a first liquid delivery unit delivering a first liquid containing an analysis object; a second liquid delivery unit delivering a second liquid not containing an analysis object; a measurement unit measuring physical properties of the delivered first liquid; first and second liquid pools containing the delivered first liquid and second liquid; and a plurality of passive valves. The apparatus further includes: a first flow passage connecting the first liquid delivery unit and the liquid delivery device; a second flow passage connecting the measurement unit and the second liquid pool; a third flow passage connecting the second liquid delivery unit and the liquid discharge unit; a first air hole provided in the first liquid pool; and a second air hole provided in the second liquid pool.

7 Claims, 10 Drawing Sheets

LIQUID DELIVERY DEVICE AND CHEMICAL ANALYSIS APPARATUS USING LIQUID DELIVERY DEVICE

CROSS-REFERENCE TO RELATED APPLICATION

The present application claims priority from Japanese Patent Application No. 2014-170030 filed on Aug. 25, 2014, the content of which is hereby incorporated by reference into this application.

TECHNICAL FIELD OF THE INVENTION

The present invention relates to a liquid delivery device for causing a liquid to flow, and a chemical analysis apparatus using the liquid delivery device.

BACKGROUND OF THE INVENTION

A liquid delivery device is a device that supplies a necessary liquid solution using a pump or others to a chemical analysis apparatus in which samples are reacted and analyzed. For example, Japanese Patent Application Laid-Open Publication No. 2005-274148 (Patent Document 1) relates to a liquid delivery device for liquid chromatography, and describes a gradient device including first flow passage, a second flow passage, a third flow passage, which each extend in predetermined directions, fourth flow passages that are n flow passages and that are connected to a Id thinner than the first flow passage, fifth flow passages that are n flow passages and that are connected to and thinner than the second flow passage, and a mixture vessel for gradient liquid (solvent) delivery for supplying gradient eluent to an analytical column while gradually changing a composition of the gradient eluent.

SUMMARY OF THE INVENTION

In a case of causing liquid to pass through only any one of a plurality of parallel-connected flow passages, for example, when the liquid is passed to flow in only any one of liquid delivery devices having a configuration in which a plurality of liquid delivery devices are connected in parallel to each other, it is required to make flow resistances of the parallel flow passages uneven by using any means. Normally, a valve is inserted into each of the parallel flow passages, and a flow passage through which the liquid is not to be passed is physically closed, so that the liquid is passed through a left flow passage. However, in this method, valving elements of the valves make contact with the liquid, and therefore, it is required to clean them in order to repeatedly use them, and this method has a large running cost.

According to the technique described in the Patent Document 1, the liquid flow is controlled by using not a normal valve which actuates a valve element but a passive valve which utilizes the flow resistance of a thin flow passage. However, in this method, while the liquid can be flowed in the mixture vessels of all the parallel-connected flow passages at the same time, the liquid cannot be flowed through only any one of the flow passages, and therefore, such a case is not taken into consideration.

An object of the present invention is to provide a liquid delivery device in which liquid can be passed selectively in only any one of parallel-connected flow passages without using the normal valve which actuates the valve element.

One aspect for solving the above-described problem provides a chemical analysis apparatus provided with a liquid delivery device including: a first liquid delivery unit that delivers a first liquid containing an object of analysis; a second liquid delivery unit that delivers a second liquid not containing the object of analysis; a measurement unit that measures physical properties of the delivered first liquid; a liquid pool that contains the delivered first liquid and second liquid; and a plurality of passive valves, and provided with a liquid discharge unit that discharges the delivered first liquid and second liquid. The liquid pool includes a first liquid pool and a second liquid pool. The apparatus further includes: a first flow passage that connects the first liquid delivery unit and the liquid delivery device; a second flow passage that connects the measurement unit and the second liquid pool; a third flow passage that connects the second liquid delivery unit and the liquid discharge unit; a first air hole provided in the first liquid pool; and a second air hole provided in the second liquid pool. The passive valve is configured of a first passive valve disposed between one end of the first liquid pool and the third flow passage, and a second passive valve disposed between the other end of the first liquid pool and one end of the second liquid pool.

According to the present invention, a liquid delivery device capable of flowing a quid selectively in only any one of parallel-connected flow passages without using a normal valve which actuates a valve element can be provided. In this manner, a structure of a liquid contact part can be simplified, so that a dead volume can be reduced.

Other problems, configurations and effects than those described above will be apparent from the following description of embodiments.

BRIEF DESCRIPTIONS OF THE DRAWINGS

DESCRIPTIONS OF THE PREFERRED EMBODIMENTS

Below, an embodiment will be described with reference to the Drawings.

(Entire Apparatus)

Figure 1:
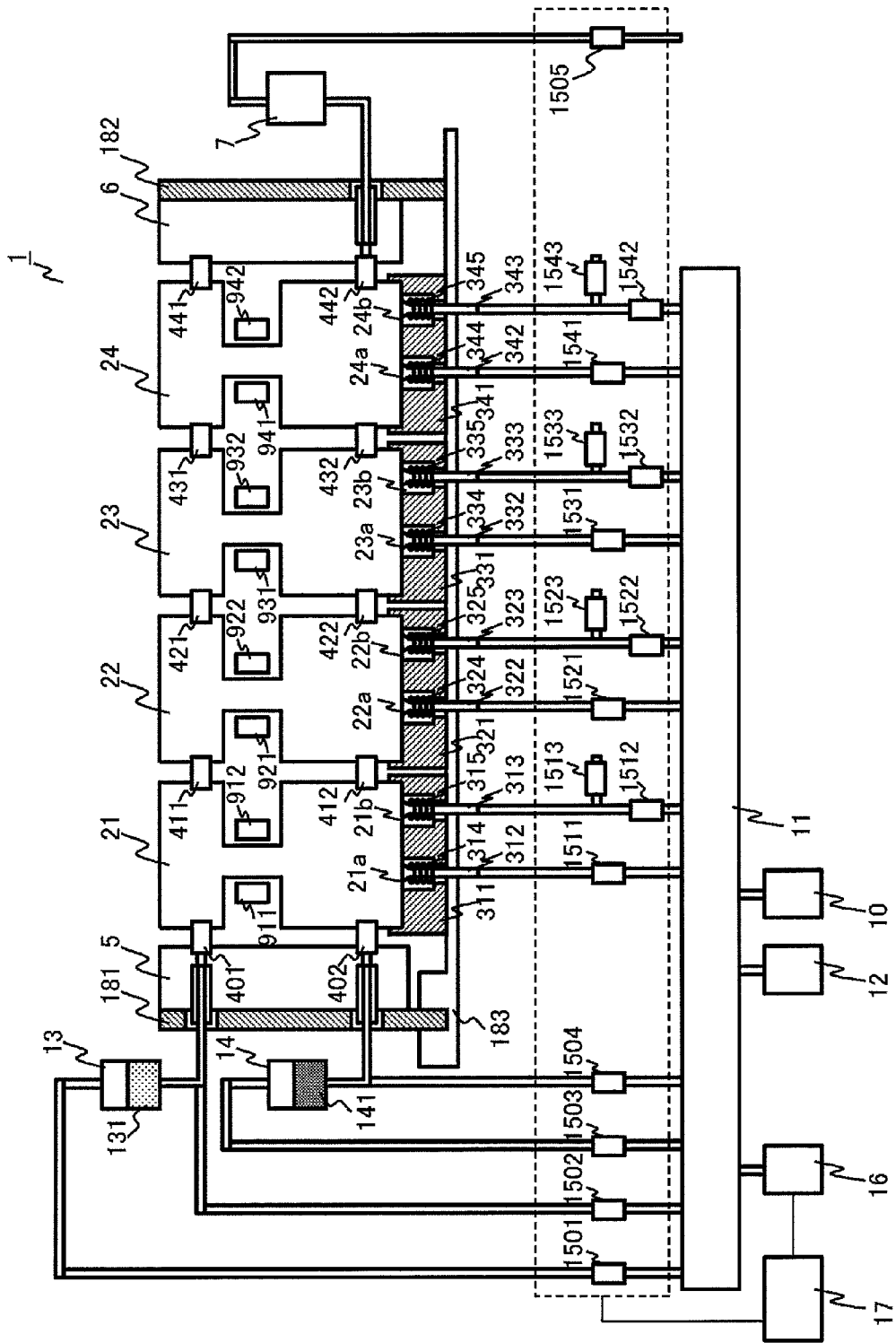
FIG. 1 is a diagram showing an example of a basic configuration of a chemical analysis apparatus according to the present embodiment.

FIG. 1 is a diagram showing an example of a basic configuration of a chemical analysis apparatus to which four liquid delivery devices according to the present embodiment, are coupled. In the chemical analysis apparatus 1 shown in this drawing, liquid delivery devices 21 to 24, a supply connector 5 that supplies a sample solution. 131 and system water 141 to the liquid delivery device 21, and a discharge connector 6 for discharging the discharged liquid from the liquid delivery device 24 to a discharged liquid tank 7 are fluidically connected to each other via packing members 401, 402, 411, 412, 421, 422, 431, 432, 441, and 442. Here, the sample solution 131 refers to a solution containing a sample that is the object of analysis, and the system water 141 refers to a liquid used for controlling passage of each sample solution 131 in the liquid delivery devices 21 to 24 as described later.

The supply connector 5 is fixed to a device-holding fixing jig 181. The discharge connector 6 is fixed to a device-holding movable jig 182. The device-holding fixing jig 181 is fixed to a guide rail 183. Meanwhile, the device-holding movable jig 182 is movable relative to the guide rail 183 in left and right directions in the drawing. When the device-holding movable jig 182 is moved to the left in the drawing, the liquid delivery devices 21 to 24, discharge connector 6, and packing members 401 to 442 are pressed against the supply connector 5.

Each of the packing members 401 to 442 is made of a material that is more flexible than materials of the supply connector 5, liquid delivery devices 21 to 24, and discharge connector 6, so that the packing members 401 to 442 are deformed when pressed, and are tightly contact with the supply connector 5, liquid delivery devices 21 to 24, and discharge connector 6, so that a pressure resistance of a fluid connection part is secured.

Air connectors 311, 321, 331, and 341 for supplying or discharging air are attached to the liquid delivery devices 21 to 24. The air connectors 311, 321, 331, and 341 are configured to be movable relative to the guide rail 183 in left and right directions in the drawing as similar to the device-holding movable jig 182. In this manner, the liquid delivery devices 21 to 24 can be pressed against the device-holding fixing jig 181 by the device-holding movable jig 182.

On lower surfaces of the liquid delivery devices 21 to 24, air inlet/outlet ports 21a, 21b, 22a, 22b, 23a, 23b, 24a, and 24b described later are provided, respectively. Air connecting parts 312 and 313 are pressed by springs 314 and 315 so as to tightly, contact with the air inlet/outlet ports 21a and 21b of the liquid delivery device 21. In this manner, high-pressure air can be introduced from an air chamber 11 into the liquid delivery device 21, or discharged from the liquid delivery device 21. Similarly, air connecting parts 322 and 323 are brought into tight contact with the air inlet/outlet ports 22a and 22b of the liquid delivery device 22, air connecting parts 332 and 333 are brought into tight contact with the air inlet/outlet ports 23a and 23b of the liquid delivery device 23, and air connecting parts 342 and 343 are brought into tight contact with the air inlet/outlet ports 24a and 24b of the liquid delivery device 24.

High-pressure air produced by a compressor 10 is retained in the air chamber 11, and is adjusted to almost constant pressure by a regulator 12. The air adjusted to a constant pressure in the air chamber 11 is fed to a sample solution container 13 via a valve 1501, to the liquid delivery devices 21 to 24 via a valve 1502 and the supply connector 5, to a system water container 14 via a valve 1503, and to the liquid delivery devices 21 to 24 via a valve 1504 and the supply connector 5. Similarly, the air in the air chamber 11 is fed to the air connecting parts 312, 313, 322, 323, 332, 333, 342, and 343 via, valves 1511, 1512, 1521, 1522, 1531, 1532, 1541, and 1542, respectively. These valves are controlled by a controller 17 to be opened for supplying the air from the air chamber 11, or to be closed for stopping the supply of the air.

Also, valves 1505, 1513, 1523, 1533, and 1543 are also controlled by the controller 17 so as to open or close each of the discharged liquid container 7 and air connecting parts 313, 323, 333, and 343 to the atmosphere.

Also, a pressure sensor 16 for measuring a pressure inside the air chamber 11 is provided. The controller 17 controls each valve so that the controller 17 adjusts the pressure based on signals supplied from the pressure sensor 16 as needed.

Physical properties such as an absorbance of a sample solution flowing through the liquid delivery devices 21 to 24 are measured by light emitting units 911, 921, 931, and 941 and light receiving units 912, 922, 932, and 942 of an optical sensor for analysis.

(Details of Liquid Delivery Device)

The liquid delivery device 21 will be described in detail with reference to FIG. 2. Note that the repetitive description of the liquid delivery devices 22, 23, and 24 will be omitted since they have the same configuration as that of the liquid delivery device 21.

Figure 2A:
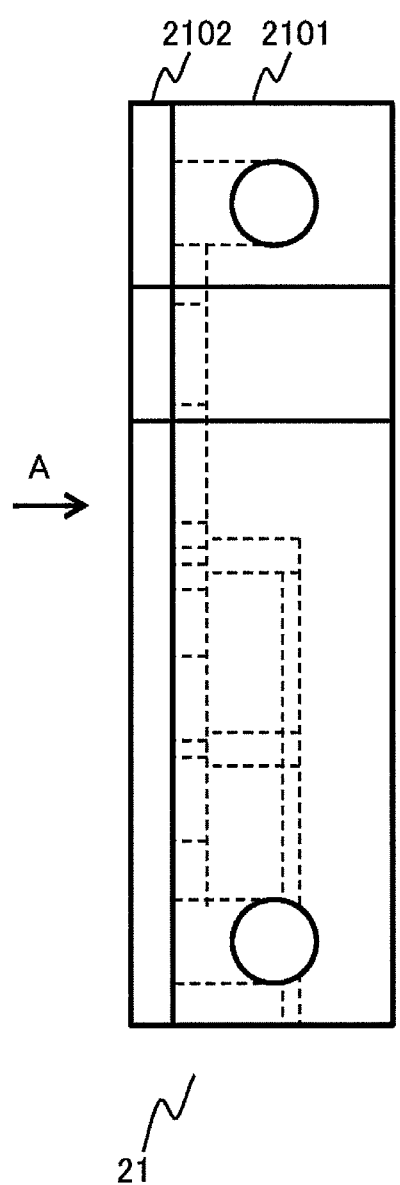
FIG. 2A is a diagram showing a side surface of a liquid delivery device according to the present embodiment.

FIG. 2A shows a side view of the liquid delivery device 21. As shown in FIG. 2A, liquid delivery device 21 is configured of a flowing unit 2101 where the flow passage is formed, and a top plate 2102 joined to the flowing unit 2101. FIG. 2A shows the flow passage formed inside the liquid delivery device 21 by a broken line.

Figure 2B:
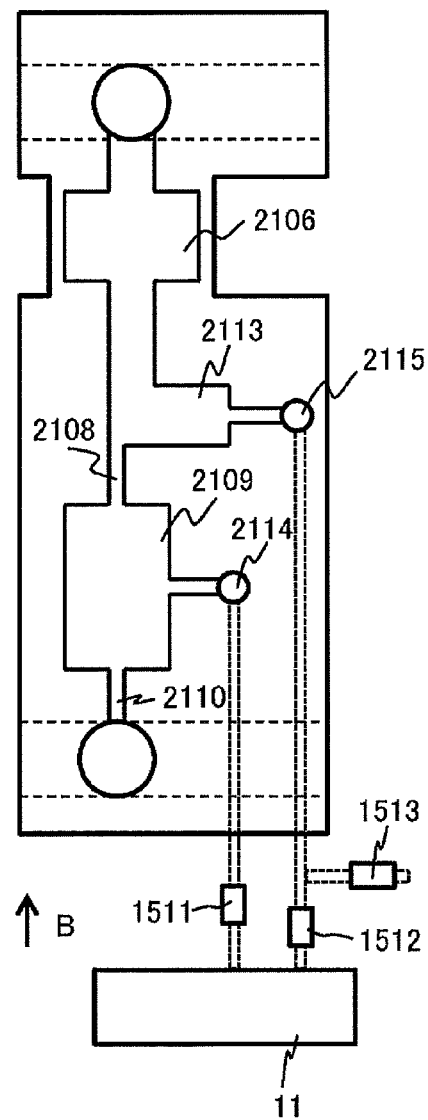
FIG. 2B is a diagram showing an upper surface of the liquid delivery device according to the present embodiment.

FIG. 2B is a top view of the liquid delivery device 21, i.e., a plan view of the flowing unit 2101 when seen from a direction of an arrow A in FIG. 2A. This drawing shows a state in which the top plate 2102 is removed, and therefore, shows the flow passage on the top plate 2102 side with a solid line, and the flow passage inside with a broken line. As shown in this drawing, the liquid delivery device 21 is provided with a first liquid pool 2109 and a second liquid pool 2113 for storing the sample solution 131 fed from the sample solution container 13 or the system water 141 fed from the system water container 14. Passive valves 2108 and 2110 are connected to both ends of the first liquid pool 2109, respectively. A first air hole 2114 is provided between connecting parts at which the first liquid pool 2109 and each of the passive valves 2108 and 2110 are connected to each other. Further, one end of the second liquid pool 2113 is connected to the passive valve 2108 that is connected to the first pool 2109, and the other end thereof has a second air hole 2115 provided thereto.

Figure 2C:
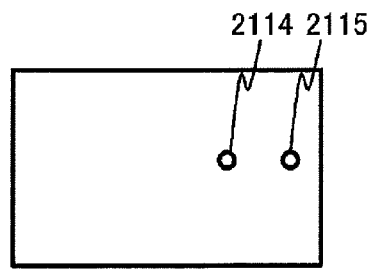
FIG. 2C is a diagram showing a lower surface of the liquid delivery device according to the present embodiment.

FIG. 2C is a bottom view of the liquid delivery device 21, i.e., a plan view of the flowing unit 2101 when seen from a direction of an arrow B in FIG. 2B. As shown in this drawing, the first air hole 2114 and second air hole 2115 are provided, and the air in the air chamber 11 is introduced from the air connecting parts 312 and 313 to the first air hole 2114 and second air hole 2115 via the valves 1511 and 1512. On the other hand, the air inside the liquid delivery device 21 is discharged from the second air hole 2115 to the atmosphere via the air connecting part 313 (not shown in this drawing) and the valve 1513. A sample measurement unit 2106 is provided with the above-described light emitting units 911 and 912 of the optical sensor, and measures and analyzes the physical properties such as absorbance of the delivered sample solution 131.

As materials for the flowing unit 2101 and top plate 2102, resin, glass, silicone, silicone rubber, metal, and others are cited. If the resin is used for the flowing unit 2101 and top plate 2102, the resin of each of them is formed by injection molding, hot embossing, cutting, or others, and bonded to each other by thermal adhesion. If the glass is used for the flowing unit 2101 and top plate 2102, each of them is formed by injection molding, and bonded to each other by thermal adhesion. Also, the flowing unit 2101 is manufactured from silicone by lithography, and bonded to a top plate made of glass by anodic bonding. Further, the flowing unit 2101 is manufactured from silicone rubber such as polydimethylsiloxane, and bonded to a top plate made of glass by surface activation bonding using plasma irradiation. If the metal is used for the flowing unit 2101 and top plate 2102, each of them is formed by cutting, and bonded to each other by diffusion bonding or brazing.

Also, the flowing unit 2101 and the top plate 2102 may be bonded to each other by interposing a thin adhesive sheet or adhesive material between the flowing unit 2101 and the top plate 2102. In this case, the flowing unit 2101 and top plate 2102 can be manufactured from any material.

Instead of separately manufacturing the flowing unit 2101 and top plate 2102 and bonding them to each other, they can be manufactured as an integrated object by a laminating molding technique such as a stereolithography method, a fused deposition modeling method, a selective laser sintering (powder sintering) method, and an inkjet method.

Each shape of the liquid delivery devices 21 to 24 is formed so as to be connectable, so that they can be fluidically connected with each other by the method described above with reference to FIG. 1. Therefore, the materials of the liquid delivery devices 21 to 24 can be different from each other, so that suitable materials can be selected in accordance with the detection method.

While the analysis apparatus is configured by combining a plurality of liquid delivery devices 21 to 24 in FIG. 1, a similar flow passage configuration may be manufactured inside one liquid delivery device. In this case, such a flexible apparatus configuration as change in the material of the flow passage in accordance with the detection method cannot be adopted. However, the packing members for connecting the liquid delivery devices are unnecessary, so that the apparatus can be downsized and simplified, so that the dead volume is reduced.

(Flowing Movements)

With reference to FIG. 3 to FIG. 14, the flowing movements of liquids and air will be explained in a case in which the sample solution 131 is measured and analyzed by optical sensors 921 and 922 in the chemical analysis apparatus 1 while the sample solution 131 is flowed to only a sample solution measurement unit 2206 of the liquid delivery device 22. FIG. 3 to FIG. 14 are simplified drawings of FIG. 1 so as to show only the fluid flowing part.

Figure 3:
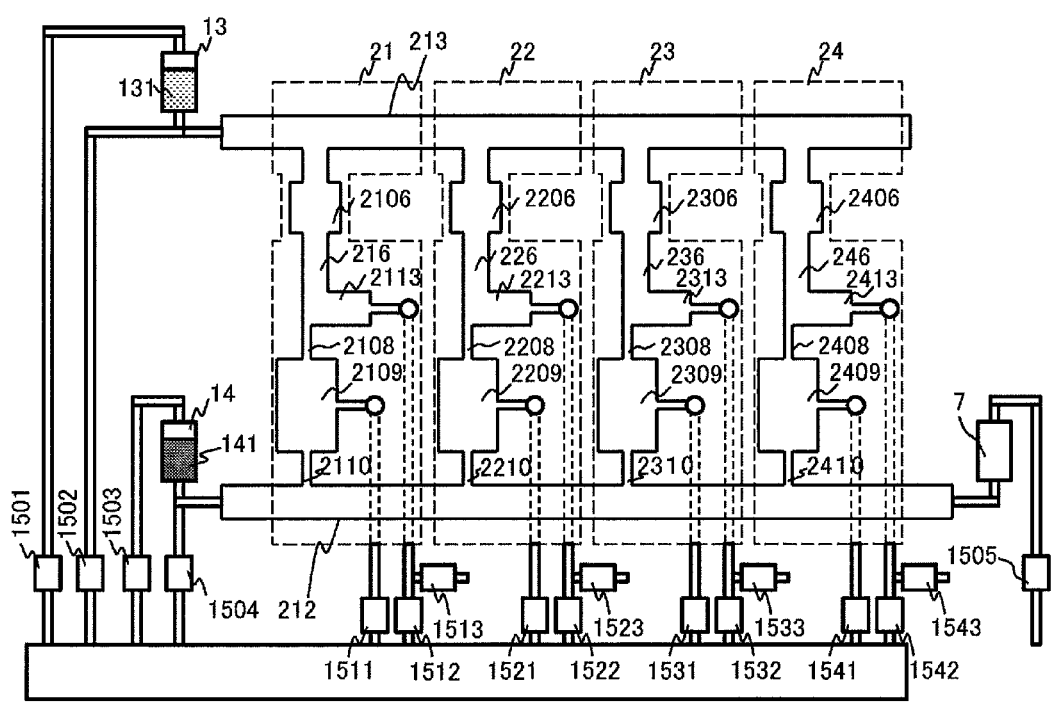
FIG. 3 is a diagram explaining an example of flowing movements of the liquid in the chemical analysis apparatus according to the present embodiment.

FIG. 3 shows an initial state. The sample solution 131 is contained in the sample solution container 13, and the system water 141 is contained in the system water container 14, and air is filled in other flow passages. All the valves 1501, 1502, 1503, 1504, 1505, 1511, 1512, 1513, 1521, 1522, 1523, 1531, 1532, 1533, 1541, 1542, and 1543 are closed. Here, it is assumed that the flow passage for supplying the sample solution 131 from the sample solution container 13 which is the supply source of the sample solution 131 to each of the liquid delivery devices 21 to 24 is a "first flow passage 213", that the flow passage that connects the sample measurement unit 2206 and the second liquid pool 2213 with each other is a "second flow passage 216", and that the flow passage that connects the system water container 14 which is the supply source of the system water 141, the liquid delivery devices 21 to 24 and the discharged liquid tank 7 with one another is a "third flow passage 212".

Figure 4:
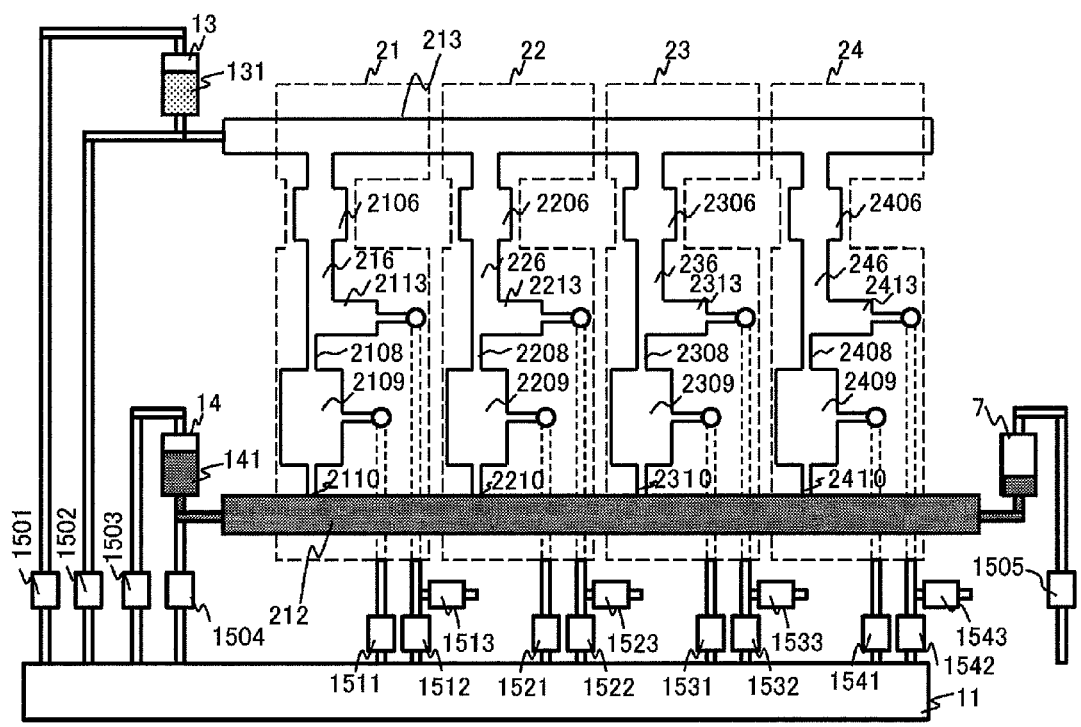
FIG. 4 is a diagram explaining an example of flowing movements of the liquid in the chemical analysis apparatus according to the present embodiment.

FIG. 4 shows a state in which the system water 141 has been introduced into the third flow passage 212. By opening the valves 1503 and 1505, the high-pressure air in the air chamber 11 is supplied to the system water container 14 to push the system water 141 out. The pushed-out system water 141 flows through the third flow passage 212 and into the discharged liquid tank 7. The air that has existed inside the flow passage before the flow of the system water 141 passes through the open valve 1505 and is discharged to the atmosphere.

Figure 5:
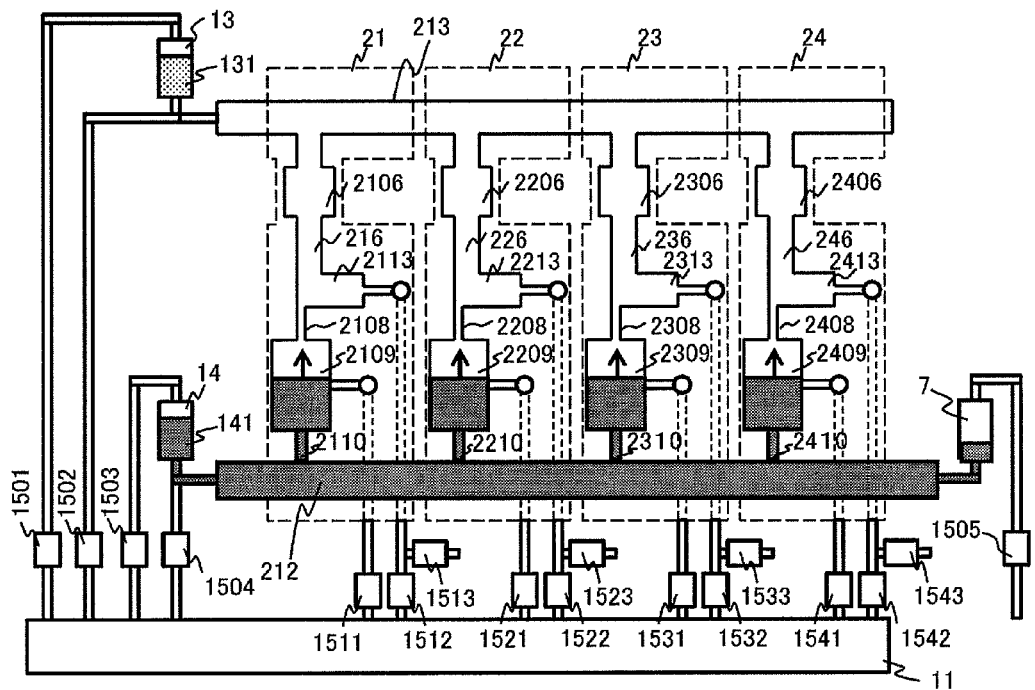
FIG. 5 is a diagram explaining an example of flowing movements of the liquid in the chemical analysis apparatus according to the present.

FIG. 5 shows a state in which the system water 141 is filled in each of the first liquid pools 2109, 2209, 2309, and 2409 of the liquid delivery devices 21 to 24. By opening the valves 1503, 1513, 1523, 1533, and 1543, the high-pressure air in the air chamber 11 is supplied to the system water container 14 to push the system water 141 out. The pushed-out system water 141 passes through the first passive valves 2110, 2210, 2310, and 2410 and flows into each of the first pools 2109, 2209, 2309, and 2409. The air that has existed inside the flow passage before the flow of the system water 141 passes through the valves 1513, 1523, 1533, and 1543 and is discharged to the atmosphere.

Each of the first passive valves 2110, 2210, 2310, and 2410 has an extremely smaller flow passage width than those of other flow passages or pipes. Accordingly, when the liquid passes through them, the flow resistances of the first passive valves 2110, 2210, 2310, and 2410 becomes dominant to other flow passages or pipes. Therefore, in the case of FIG. 5, a magnitude of the flow resistance of the third flow passage 212 is negligible compared to the flow resistances of the passive valves 2110, 2210, 2310, and 2410. As a result, the system water 141 is filled in the first liquid pools 2109, 2209, 2309, and 2409 with almost the same flow amount.

Figure 6:
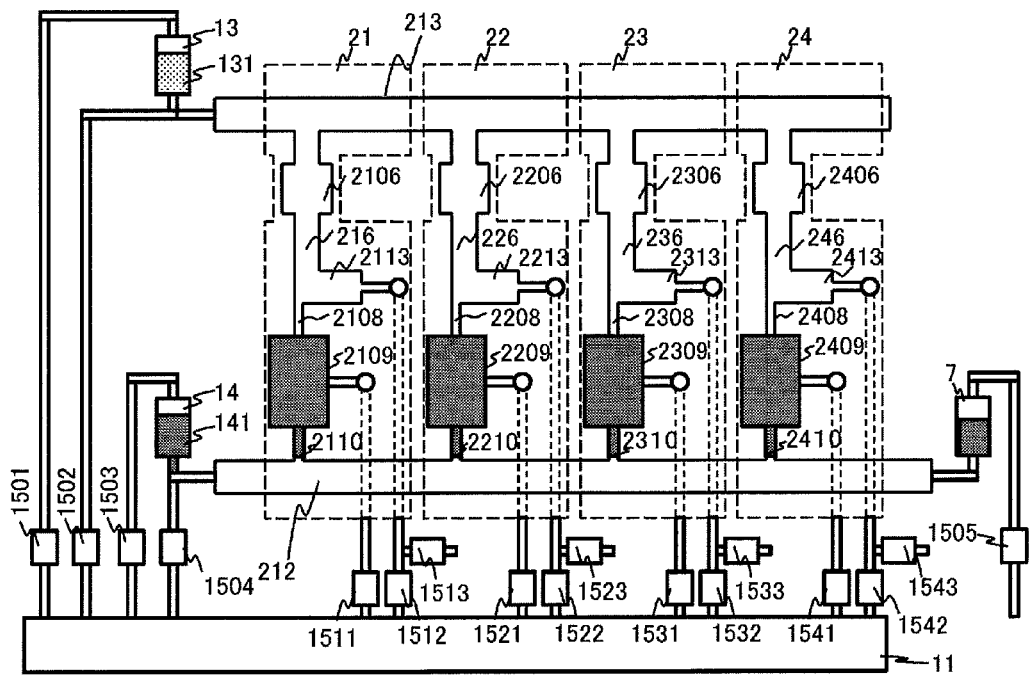
FIG. 6 is a diagram explaining an example of flowing movements of the liquid in the chemical analysis apparatus according to the present.

FIG. 6 shows a state in which the system water 141 is filled in the first liquid pools 2109, 2209, 2309, and 2409, and then, the high-pressure air in the air chamber 11 is supplied into the third flow passage 212 by opening the valves 1504 and 1505 to discharge the system water 141 into the discharged liquid tank 7.

Figure 7:
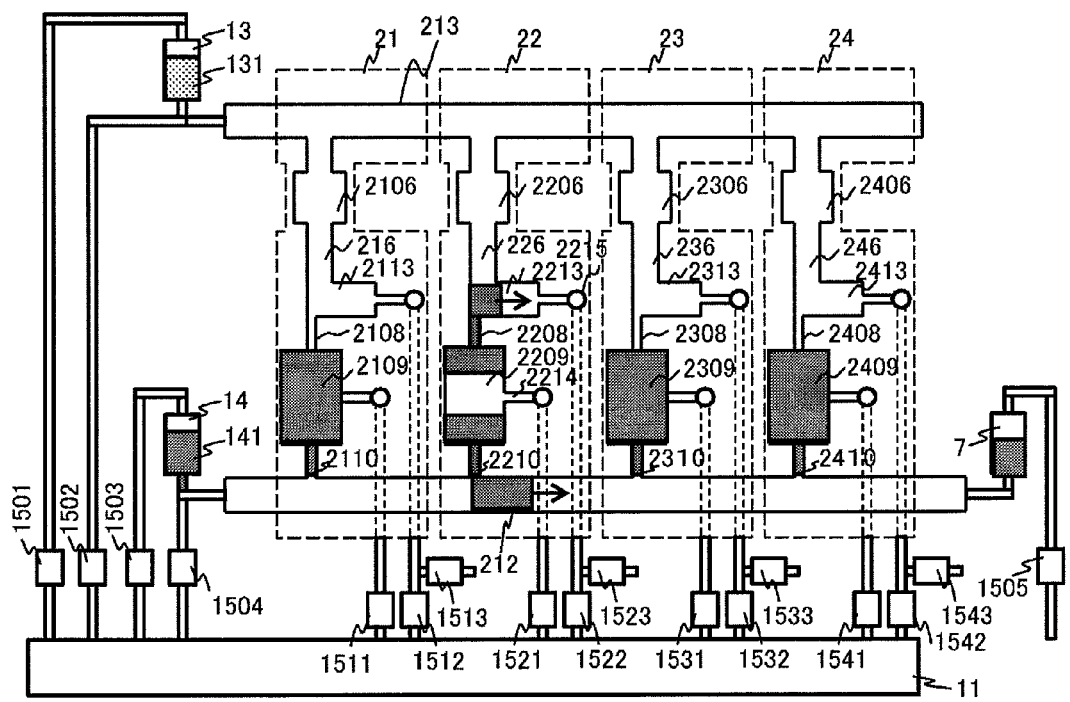
FIG. 7 is a diagram explaining en example of flowing movements of the liquid in the chemical analysis apparatus according to the present.

FIG. 7 shows a state in which the system water 141 filled in the first liquid pool 2209 of the liquid delivery device 22 is divided in two directions and is discharged. By opening the valves 1505, 1521, and 1523, the high-pressure air in the air chamber 11 passes through a first air flow passage 2214 and is supplied into the first pool 2209. The half of the system water 141 pushed out by the supplied high-pressure air passes through the first passive valve 2210 and is discharged into the third flow passage 212. At the same time, the rest of the half of the system water 141 passes through the second passive valve 2208 and is discharged into the second liquid pool 2213. The air that has existed inside the flow passage before the flow of the system water 141 passes through the valves 1505 and 1523 and is discharged to the atmosphere.

The first passive valve 2210 and second passive valve 2208 have the same shape as each other, and therefore, have the same flow resistance as each other. As described above, when the liquid flows, the flow resistance of the passive valves is dominant. Therefore, in the case of FIG. 7, the flow amount of the system water 141 discharged through the first passive valve 2210 and the flow amount of the system water 141 flowing on the second liquid pool 2213 side are almost equal to each other. And, the first air flow passage 2214 is set in the center of the first liquid pool 2209. Therefore, the time for discharging the system water 141 from the first passive valve 2210 and the time for discharging the system water 141 from the second passive valve 2208 are almost equal to each other.

Figure 8:
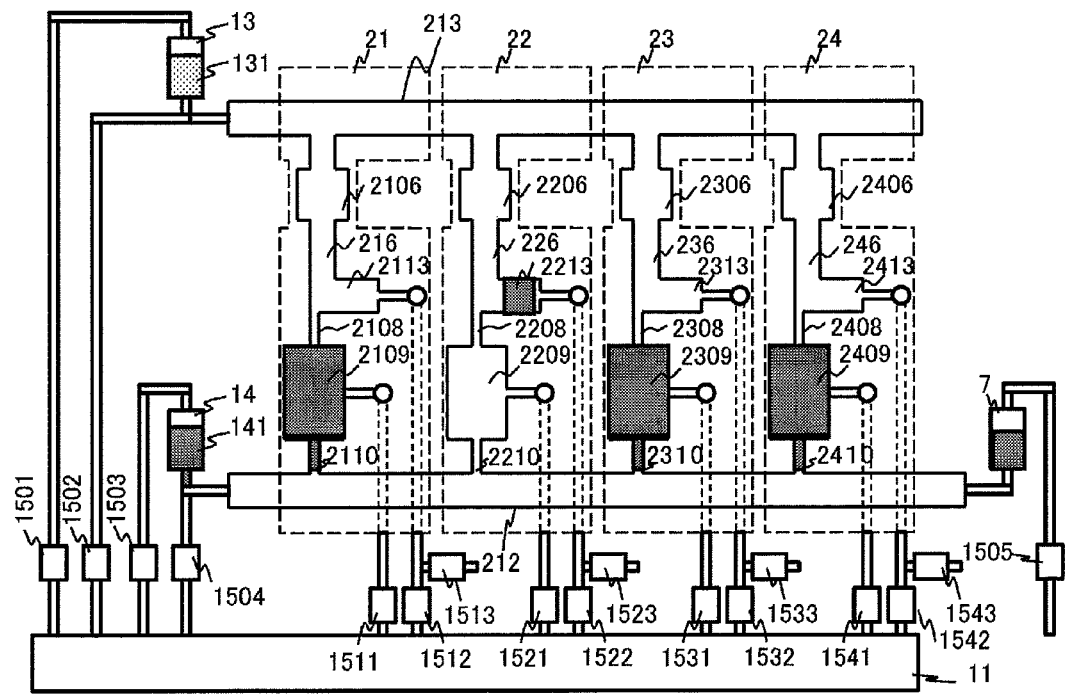
FIG. 8 is a diagram explaining an example of flowing movements of the liquid in the chemical analysis apparatus according to the present.

FIG. 8 shows a state in which the system water 141 is discharged from the first liquid pool 2209 into the third flow passage 212 and the second liquid pool 2213, and then, the system water in the third flow passage 212 is discharged into the discharged liquid tank 7. As has been described with reference to FIG. 6, the high-pressure air in the air chamber 11 is supplied into the third flow passage 212 by opening the valves 1504 and 1505 to discharge the system water 141 into the discharged liquid tank 7.

Figure 9:
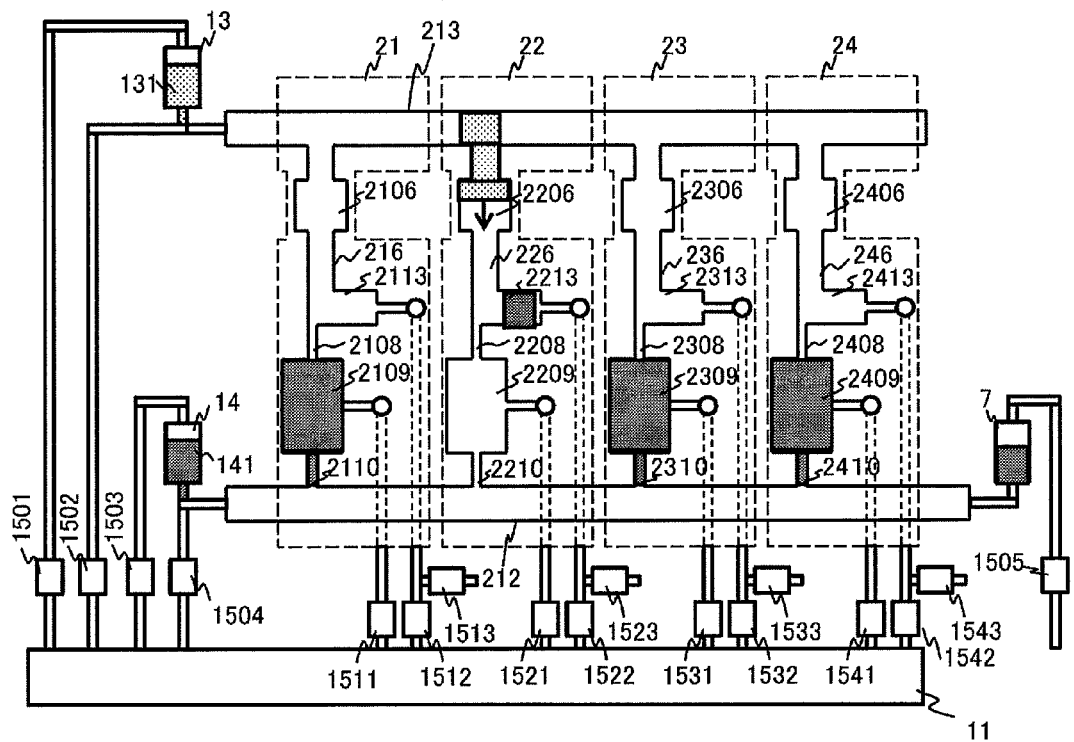
FIG. 9 is a diagram explaining an example of flowing movements of the liquid in the chemical analysis apparatus according to the present.

FIG. 9 shows a state in which the sample solution 131 is filled in the sample measurement unit 2206 of the liquid delivery device 22. First, the high-pressure air in the air chamber 11 is supplied to the sample solution container 13 by opening the valves 1501 and 1505 to push the sample solution 131 out toward the liquid delivery devices 21 to 24 side. When a predetermined volume of the sample solution 131 is pushed out, by closing the valve 1501 but opening the valve 1502, the sample solution 131 pushed out from the sample solution container 13 is introduced into the liquid delivery device 22.

In this drawing, the air that has existed in the first flow passage 213 before the introduction of the sample solution 131 is pushed out by the sample solution 131, and is introduced into the liquid delivery device 22 through the first flow passage 213, moves to the discharged liquid tank 7 and the valve 1505 through the second flow passage 226 and the third flow passage 212, and is discharged to the atmosphere. At this time, while the air is filled entirely inside the liquid delivery device 22 except for the second liquid pool 2213, the system water 141 is filled in the first liquid pools 2109, 2309 and 2409 of the liquid delivery devices 21, 23, and 24. The air has a much lower viscosity than a viscosity of the liquid, and therefore, even if the high-pressure air is supplied from the air chamber 11, the air flows only into the liquid delivery device 22 but is hardly supplied to the liquid delivery devices 21, 23, and 24. As a result, the sample solution 131 is selectively supplied only to the sample measurement unit 2206 of the liquid delivery device 22.

Figure 10:
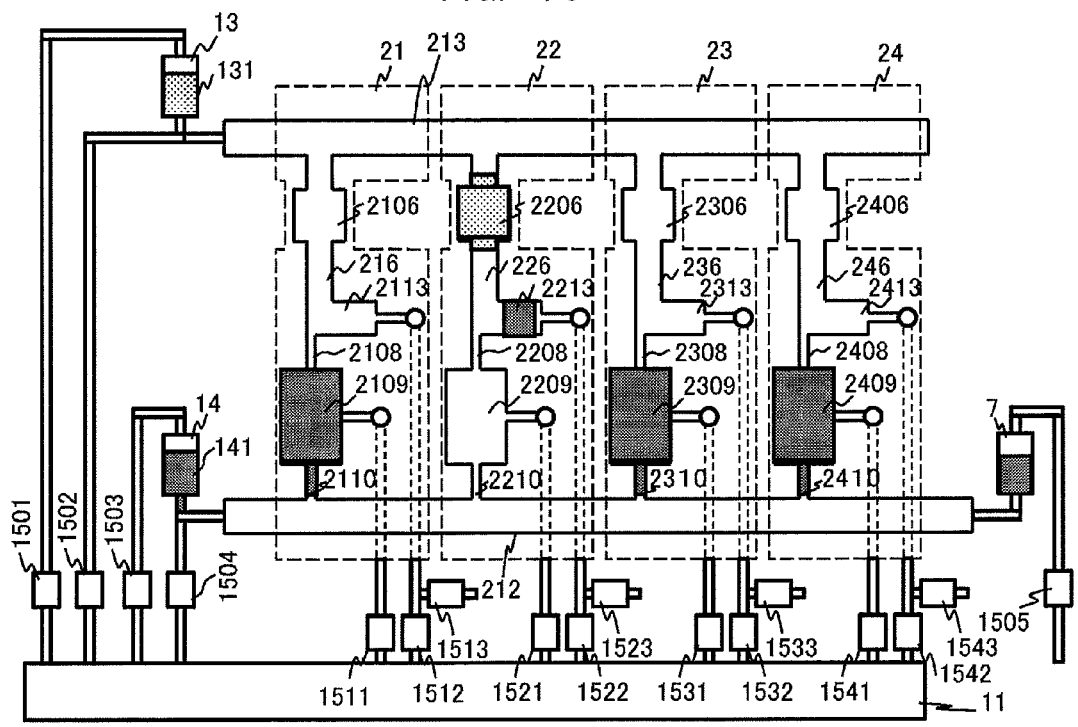
FIG. 10 is a diagram explaining an example of flowing movements of the liquid in the chemical analysis apparatus according to the present.

FIG. 10 shows a state in which the sample solution 131 is filled in the sample measurement unit 2206 of the liquid delivery device 22. At this time, the valves 1501, 1502, 1503, 1504, 1505, 1511, 1512, 1513, 1521, 1522, 1523, 1531, 1532, 1533, 1541, 1542, and 1543 are all closed, the sample solution 131 remains stationary in the sample measurement unit 2206 and is measured by the optical sensors 921 and 922 (see FIG. 1).

Figure 11:
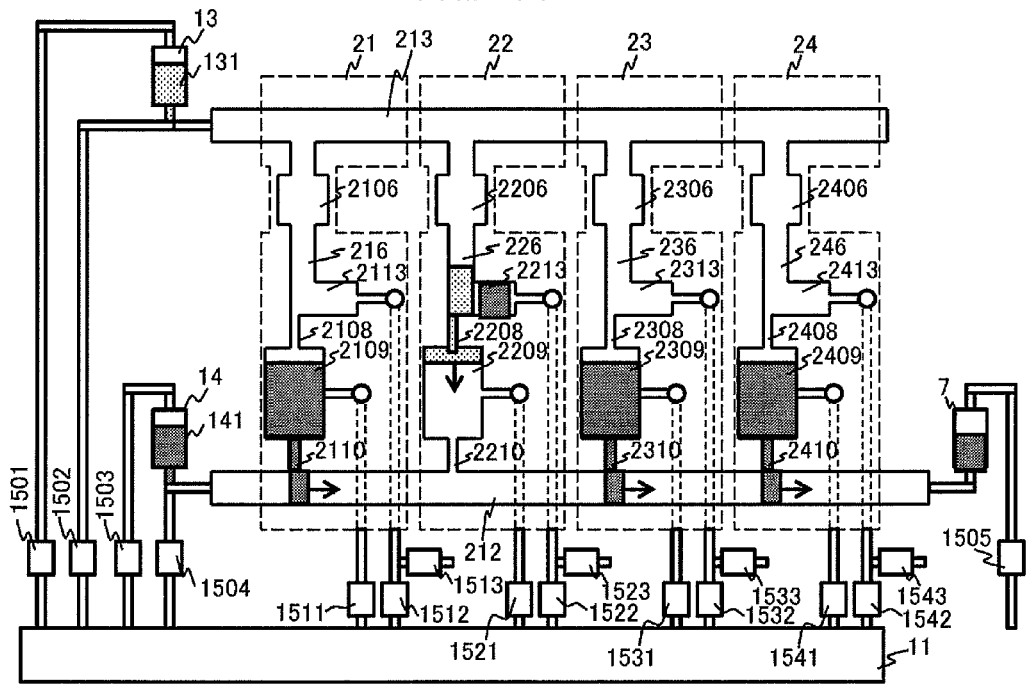
FIG. 11 is a diagram explaining an example of flowing movements of the liquid in the chemical analysis apparatus according to the present.

FIG. 11 shows a state in which the sample solution 131 that has existed inside the sample measurement unit 2206 is discharged into the first liquid tool 2209. By opening the valves 1502 and 1505, the high-pressure air in the air chamber 11 passes through the first flow passage 213 and is supplied to the first pools 2109, 2309, and 2409, and to the sample measurement unit 2206. The system water 141 that has existed in the first pools 2109, 2309, and 2409 passes through the first passive valves 2110, 2310, and 2410 and is discharged into the third flow passage 212. The sample solution that has existed inside the sample measurement unit 2106 passes through the second passive valve 2208 and is discharged into the first liquid pool 2209. At this time, the first passive valves 2110, 2310, and 2410, and the second passive valve 2208 have the same shape and the same flow resistance as one another, and therefore, have almost the same flow amount flowing in each of them. The air that has existed inside the flow passage before the supply of the high-pressure air is discharged into the atmosphere through the valve 1505.

Figure 12:
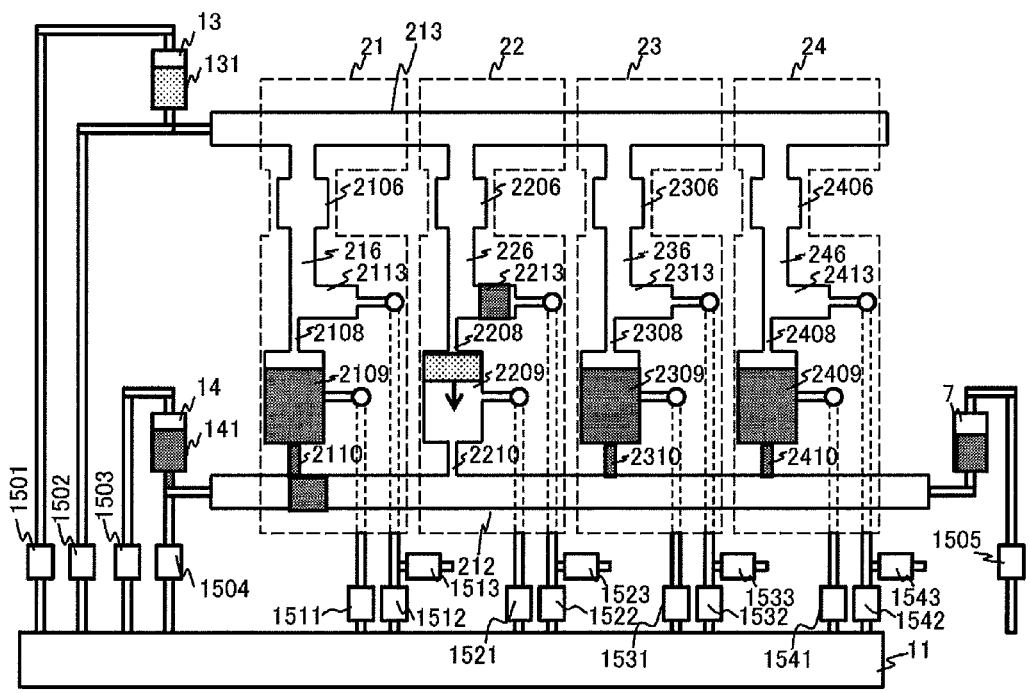
FIG. 12 is a diagram explaining an example of flowing movements of the liquid in the chemical analysis apparatus according to the present.

FIG. 12 shows a state in which the sample solution 131 that has existed inside the sample measurement unit 2206 is discharged completely into the first liquid pool 2209. In this state, the valves 1502 and 1505 are still opened as continued from the state of FIG. 11, the high-pressure air in the air chamber 11 is supplied to the first liquid pools 2109, 2209, 2309, and 2409. However, the flow resistance caused when the sample solution 131 flows in the first pool 2209 is much smaller than the flow resistance caused when the system water 141 flows in the first passive valves 2110, 2310, and 2410. Therefore, the system water 141 in the first passive valves 2210, 2310, and 2410 hardly flows, and only the sample solution 131 in the first liquid pool. 2209 flows. At this time, the system water 141 pushed out from the first liquid pools 2309 and 2409 into the third flow passage 212 in the state of FIG. 11 is pushed and flowed from the first liquid pool 2209 toward the discharged liquid tank 7 by the discharged air.

Figure 13:
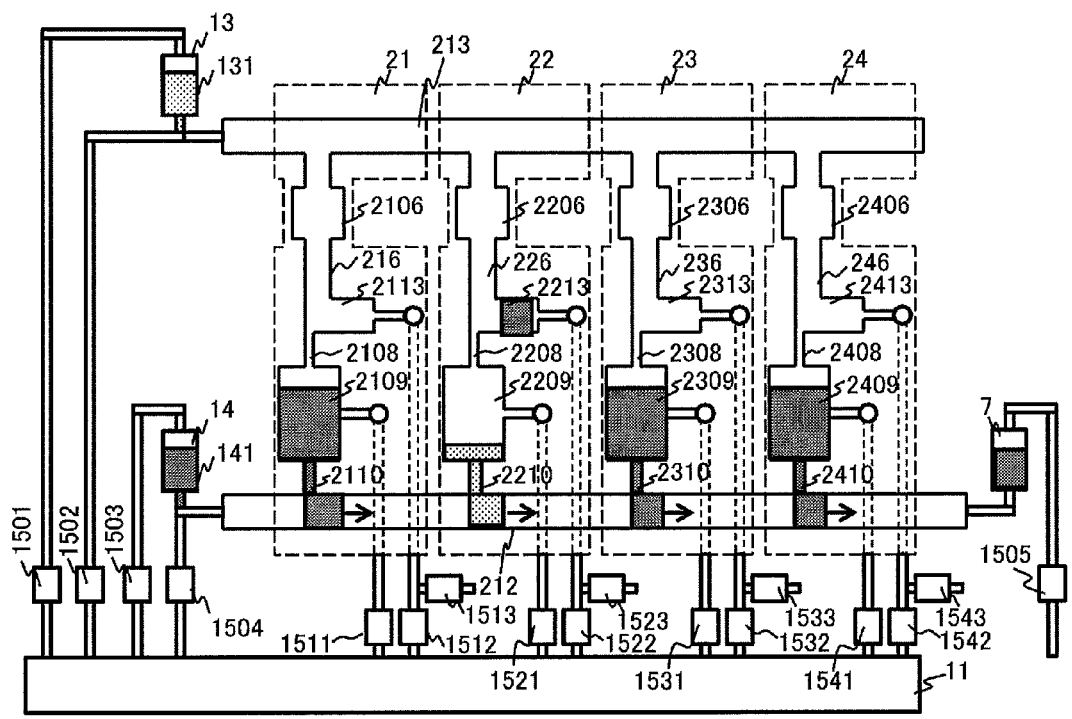
FIG. 13 is a diagram explaining an example of flowing movements of the liquid in the chemical analysis apparatus according to the present.

FIG. 13 shows a state in which the sample solution 131 that has existed in the first liquid pool 2209 is discharged into the third flow passage 212 through the first passive valve 2210. Since the valves 1502 and 1505 are still opened as continued from the state of FIG. 12, the high-pressure air in the air chamber 11 is supplied to the first liquid pools 2109, 2209, 2309, and 2409. Therefore, the system water 141 in the first liquid pools 2109, 2309, and 2409 is also discharged into the third flow passage 212 through the first passive valves 2210, 2310, and 2410. At this time, the flow resistances of the first passive valves 2110, 2210, 2310, and 2410 are dominant, and therefore, the liquid flows through each of them has the same flow amount as each other.

Figure 14:
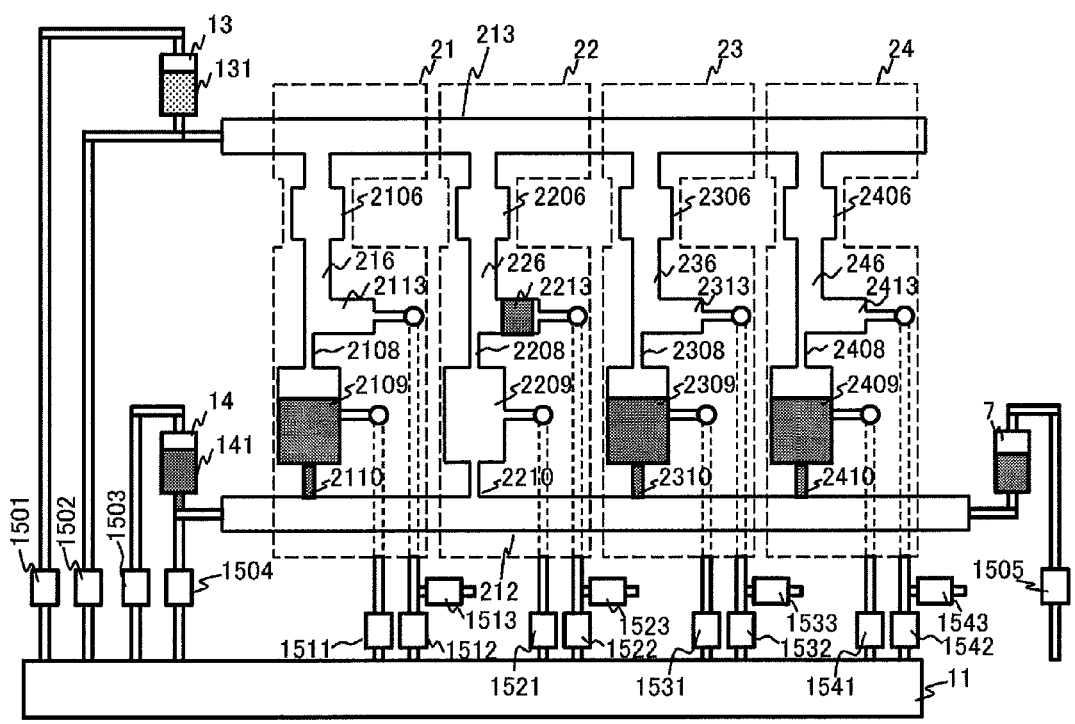
FIG. 14 is a diagram explaining an example of flowing movements of the liquid in the chemical analysis apparatus according to the present embodiment.

FIG. 14 shows a state in which the sample solution 131 an the first liquid pool 2209 is discharged completely into the third flow passage 212, and then, the system water 141 and sample solution 131 in the third flow passage 212 are discharged into the discharged liquid tank 7. As has been described with reference to FIG. 6, the high-pressure air in the air chamber 11 is supplied into the third flow passage 212 by opening the valves 1504 and 1505 to discharge the system water 141 and sample solution 131 into the discharged liquid tank 7.

As described above, by causing the air to flow from the first air flow passage 2215 set in the center of the first liquid pool 2209, the system water 141 filled in the first liquid pool 2209 is divided and discharged, so that the sample solution 131 can selectively be filled in and discharged from only one of the parallel-connected sample measurement units 2106, 2206, 2306, and 2406. At this time, the liquid does not contact the valves which actuate the valve elements, and the valves are used only for supplying and discharging the air, and therefore, the flowing passage configuration the valves do not need to be cleaned less, and have less frequency of the replacement than those in the flow passage configuration in which the liquid contacts the valves, and therefore, the running cost of the analysis apparatus can be reduced.

What is claimed is:

1. A chemical analysis apparatus comprising:
   a first liquid delivery unit that delivers a first liquid containing an object of analysis;
   a second liquid delivery unit that delivers a second liquid not containing an object of analysis;
   a liquid delivery device including a measurement unit that measures physical properties of the delivered first liquid, a liquid pool that contains the delivered first liquid and second liquid, and a plurality of passive valves; and
   a liquid discharge unit that discharges the delivered first liquid and second liquid,
   wherein the liquid pool includes a first liquid pool and a second liquid pool,
   the apparatus further includes:
      a first flow passage that connects the first liquid delivery unit and the liquid delivery device;
      a second flow passage that connects the measurement unit and the second liquid pool;
      a third flow passage that connects the second liquid delivery unit and the liquid discharge unit;
      a first air hole provided in the first liquid pool; and
      a second air hole provided in the second liquid pool, and
   the passive valves include a first passive valve disposed between one end of the first liquid pool and the third flow passage, and a second passive valve disposed between the other end of the first liquid pool and one end of the second liquid pool.

2. The chemical analysis apparatus according to claim 1, wherein the first flow passage, the second flow passage, and the third flow passage are fluidically connected with each other.

3. The chemical analysis apparatus according to claim 1, wherein a flow resistance of the first passive valve and a flow resistance of the second passive valve are substantially the same as each other.

4. The chemical analysis apparatus according to claim 1, wherein the first air hole is provided between a connecting part between one end of the first liquid pool and the first passive valve, and a connecting part between the other end of the first liquid pool and the second passive valve.

5. The chemical analysis apparatus according to claim 1, wherein the apparatus includes a plurality of the liquid delivery devices, and
the plurality of liquid delivery devices are connectable to each other.

6. The chemical analysis apparatus according to claim 1, wherein the second liquid is system water.

7. The chemical analysis apparatus according to claim 1, further comprising
an air chamber that stores high-pressure air,
wherein the first liquid delivery unit and the second liquid delivery unit deliver each of the first liquid and the second liquid by air supply from the air chamber.

* * * * *